United States Patent
Steiner et al.

[11] Patent Number: 6,159,981
[45] Date of Patent: Dec. 12, 2000

[54] 3-SUBSTITUTED PYRIDO [3',4':4,5] THIENO [2,3-D] PYRIMIDINE DERIVATIVES, AND PRODUCTION AND USE OF THE SAME

[75] Inventors: Gerd Steiner, Kirchheim; Uta Dullweber, Frankenthal; Dorothea Starck, Ludwigshafen; Alfred Bach, Heidelberg; Karsten Wicke, Altrip; Hans-Jürgen Teschendorf, Dudenhofen; Francisco-Javier Garcia-Ladona, Kandel; Franz Emling, Ludwigshafen, all of Germany

[73] Assignee: BASF Aktiengesellschaft, Ludwigshafen, Germany

[21] Appl. No.: 09/445,178

[22] PCT Filed: May 29, 1998

[86] PCT No.: PCT/EP98/03231

§ 371 Date: Dec. 8, 1999

§ 102(e) Date: Dec. 8, 1999

[87] PCT Pub. No.: WO98/56793

PCT Pub. Date: Dec. 17, 1998

[30] Foreign Application Priority Data

Jun. 13, 1997 [DE] Germany .................. 197 24 979

[51] Int. Cl.[7] .................. A61K 31/495; A61K 31/505
[52] U.S. Cl. .................. 514/255; 514/212; 514/267; 544/250; 540/600
[58] Field of Search .................. 544/250; 540/600; 514/212, 255, 267

[56] References Cited

U.S. PATENT DOCUMENTS 4,835,157 5/1989 Press et al. .................. 514/258

FOREIGN PATENT DOCUMENTS 329 168 8/1989 European Pat. Off. .
98/11110 3/1998 WIPO .

Primary Examiner—Amelia Owens
Attorney, Agent, or Firm—Keil & Weinkauf

[57] ABSTRACT

3-Substituted 3,4,5,6,7,8-hexahydropyrido [3',4':4,5]-thieno [2,3-d]pyrimidine derivatives of the formula I

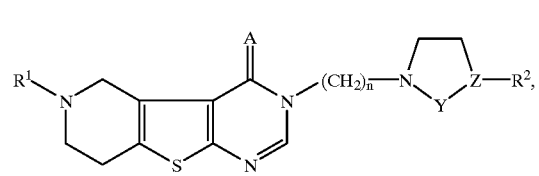

where $R^1$ is a hydrogen atom, a $C_1$–$C_4$-alkyl group, an acetyl group, a phenylalkyl $C_1$–$C_4$ radical, the aromatic system being unsubstituted or substituted by halogen, $C_1$–$C_4$-alkyl, trifluoromethyl, hydroxyl, $C_1$–$C_4$-alkoxy, amino, cyano or nitro groups, or is a phenylalkanone radical, it being possible for the phenyl group to be substituted by halogen, $R^2$ is a phenyl, pyridyl, pyrimidinyl or pyrazinyl group which is unsubstituted or mono- or disubstituted by halogen atoms, $C_1$–$C_4$-alkyl, trifluoromethyl, trifluoromethoxy, hydroxyl, $C_1$–$C_4$-alkoxy, amino, monomethylamino, dimethylamino, cyano or nitro groups and which may be fused to a benzene nucleus which can be unsubstituted or mono- or disubstituted by halogen atoms, $C_1$–$C_4$-alkyl, hydroxyl, trifluoromethyl, $C_1$–$C_4$-alkoxy, amino, cyano or nitro groups and may contain 1 nitrogen atom, or to a 5- or 6-membered ring which may contain 1–2 oxygen atoms, A is NH or an oxygen atom, Y is $CH_2$, $CH_2$—$CH_2$, $CH_2$—$CH_2$—$CH_2$ or $CH_2$—CH, Z is a nitrogen atom, carbon atom or CH, it also being possible for the linkage between Y and Z to be a double bond, and n is 2, 3 or 4, and the physiologically tolerated salts thereof.

7 Claims, No Drawings

3-SUBSTITUTED PYRIDO [3',4':4,5] THIENO [2,3-D] PYRIMIDINE DERIVATIVES, AND PRODUCTION AND USE OF THE SAME

The invention relates to novel 3-substituted pyrido[3', 4':4,5]thieno[2,3-d]pyrimidine derivatives, their preparation and use for producing active ingredients for drugs.

Classical antidepressants, and the newer selective serotonin reuptake inhibitors (SSRIs) develop their antidepressent effect inter alia by inhibiting active reuptake of the transmitter into the presynaptic nerve endings. Unfortunately, the antidepressant effect thereof does not have its onset until treatment has lasted at least 3 months, and, moreover, about 30% of patients are therapy-resistant.

Blockade of presynaptic serotonin autoreceptors increases, by abolishing negative coupling, the serotonin release and thus the current transmitter concentration in the synaptic cleft. This increase in the transmitter concentration is regarded as the principle of the antidepressant effect. This mechanism of action differs from previously known antidepressants which activate both the presynaptic and somatodendritic autoreceptors and therefore result in a delayed onset of action, only after desensitization of these autoreceptors. Direct autoreceptor blockade bypasses this effect.

According to current knowledge, the presynaptic serotonin autoreceptor is of the 5-$HT_{1B}$ subtype (Fink et al., Arch. Pharmacol. 352 (1995), 451). Selective blockade thereof by 5-$HT_{1B/D}$ antagonists increases serotonin release in the brain: G. W. Price et al., Behavioural Brain Research 73 (1996), 79–82; P. H. Hutson et al., Neuropharmacology Vol. 34, No. 4 (1995), 383–392.

However, surprisingly, the selective 5-$HT_{1B}$ antagonist GR 127 935 reduces serotonin release in the cortex after systemic administration. One explanation might be stimulation of somatodendritic 5-$HT_{1A}$ receptors in the raphe region by the released serotonin, which inhibits the firing rate of serotonergic neurons and thus serotonin release (M. Skingle et al., Neuropharmacology Vol. 34 No. 4 (1995), 377–382, 393–402).

One strategy for bypassing the autoinhibitory effects in serotonergic areas of origin thus aims at blockade of presynaptic 5-$HT_{1B}$ receptors. This hypothesis is supported by the observation that the effect of paroxetine on serotonin release in the dorsal raphe nucleus of the rat is potentiated by the 5-$HT_{1B}$ receptor antagonist GR 127 935 (Davidson and Stamford, Neuroscience Letts., 188 (1995),41).

The second strategy includes blockade of both types of autoreceptors, namely the 5-$HT_{1A}$ receptors, in order to intensify neuronal firing, and the 5-$HT_{1B}$ receptors, in order to increase terminal serotonin release (Starkey and Skingle, Neuropharmacology 33 (3–4) (1994),393).

5-$HT_{1B/D}$ antagonists, alone or coupled to a 5-$HT_{1A}$ receptor antagonistic component, should therefore cause a greater increase in serotonin release in the brain and might therefore be associated with advantages in the therapy of depressions and related psychological disorders.

It has now been found that 3-substituted 3,4,5,6,7,8 hexahydropyrido[3',4':4,5]thieno[2,3-d]pyrimidine derivatives of

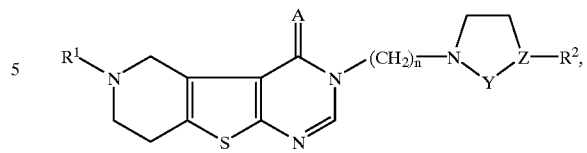

where $R^1$ is a hydrogen atom, a $C_1$–$C_4$-alkyl group, an acetyl group, a phenylalkyl $C_1$–$C_4$ radical, the aromatic system being unsubstituted or substituted by halogen, $C_1$–$C_4$-alkyl, trifluoromethyl, hydroxyl, $C_1$–$C_4$-alkoxy, amino, cyano or nitro groups, or is a phenylalkanone radical, it being possible for the phenyl group to be substituted by halogen, $R^2$ is a phenyl, pyridyl, pyrimidinyl or pyrazinyl group which is unsubstituted or mono- or disubstituted by halogen atoms, $C_1$–$C_4$-alkyl, trifluoromethyl, trifluoromethoxy, hydroxyl, $C_1$–$C_4$-alkoxy, amino, monomethylamino, dimethylamino, cyano or nitro groups and which may be fused to a benzene nucleus which can be unsubstituted or mono- or disubstituted by halogen atoms, $C_1$–$C_4$-alkyl, hydroxyl, trifluoromethyl, $C_1$–$C_4$-alkoxy, amino, cyano or nitro groups and may contain 1 nitrogen atom, or to a 5- or 6-membered ring which may contain 1–2 oxygen atoms, A is NH or an oxygen atom, Y is $CH_2$, $CH_2$—$CH_2$, $CH_2$—$CH_2$—$CH_2$ or $CH_2$—CH, Z is a nitrogen atom, carbon atom or CH, it also being possible for the linkage between Y and Z to be a double bond, and n is 2, 3 or 4, and the salts thereof with physiologically tolerated acids, have valuable pharmacological properties.

Particularly preferred compounds are those where $R^1$ is methyl, ethyl, benzyl $R^2$ is 0-methoxyphenyl, 1-naphthyl, 2-methoxy-1-naphthyl, 2-methyl-1-naphthyl A is an oxygen atom Y is $CH_2$—$CH_2$ Z is a nitrogen atom and n is 2 and 3.

The compounds of the formula I can be prepared by reacting a compound of the formula II

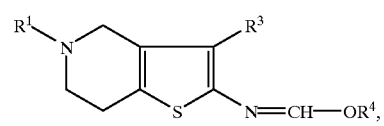

where $R_1$ [sic] has the abovementioned meaning, $R^3$ is a cyano group or a $C_{1-3}$-alkylcarboxylic ester group, and $R^4$ is $C_{1-3}$-alkyl, with a primary amine of the formula III

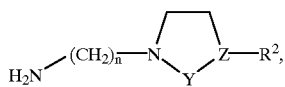

where R² has the abovementioned meaning, and converting the compound obtained in this way where appropriate into the addition salt with a physiologically tolerated acid.

The reaction is expediently carried out in an inert organic solvent, in particular a lower alcohol, e.g. methanol or ethanol, or a cyclic saturated ether, in particular tetrahydrofuran or dioxane.

The reaction is, as a rule, carried out at from 20 to 110° C., in particular from 60 to 90° C., and is generally complete within 1 to 10 hours.

Or a compound of the formula II

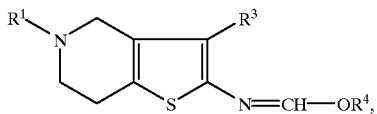

where $R_1$ [sic] has the abovementioned meaning, $R^3$ is a cyano group or a $C_{1-3}$-alkylcarboxylic ester group, and $R^4$ is $C_{1-3}$-alkyl, is reacted with a primary amino alcohol of the formula IV

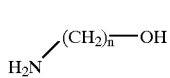

in an inert solvent, preferably alcohols such as ethanol, at from 60° to 120° C., to give the cyclization product V (X=OH)

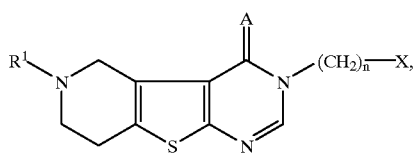

which is subsequently converted with a halogenating agent, e.g. thionyl chloride or hydrobromic acid, in an organic solvent such as a halohydrocarbon or without solvent, at from room temperature to 100° C., into the corresponding halogen derivative V (X=Cl, Br). Finally, the halogen derivative of the formula V (X=Cl, Br) is reacted with an amine of the formula VI

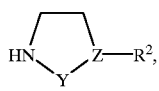

where Y, Z and R² have the abovementioned meanings, to give the novel final product of the formula I. This reaction takes place best in an inert organic solvent, preferably toluene or xylene, in the presence of a base, e.g. potassium carbonate or potassium hydroxide, at from 60° C. to 150° C.

The novel compounds of the formula I can be either recrystallized by recrystallization from conventional organic solvents, preferably from a lower alcohol such as ethanol, or purified by column chromatography.

The free 3-substituted pyrido[3',4':4,5]thieno[2,3-d]pyrimidine derivatives of the formula I can [lacuna] in a conventional way into the acid addition salts of [sic] a solution with the stoichiometric amount of the appropriate acid. Examples of pharmaceutically acceptable acids are hydrochloric acid, phosphoric acid, sulfuric acid, methanesulfonic acid, sulfamic acid, maleic acid, fumaric acid, oxalic acid, tartaric acid, or citric acid.

The invention accordingly also relates to a therapeutic composition having a content of a compound of the formula I or its pharmacologically acceptable acid addition salt as active ingredient besides conventional carriers and diluents, and to the use of the novel compounds for controlling diseases.

The novel compounds can be administered orally or parenterally, intravenously or intramuscularly, in a conventional way.

The dosage depends on the age, condition and weight of the patient and on the mode of administration. As a rule, the daily dose of active ingredient is from about 1 to 100 mg/kg of bodyweight on oral administration and from 0.1 to 10 mg/kg of bodyweight on parenteral administration.

The novel compounds can be used in conventional solid or liquid pharmaceutical forms, e.g. as uncoated or (film) coated tablets, capsules, powders, granules, suppositories, solutions, ointments, creams or sprays. These can be produced in a conventional way. The active ingredients can for this purpose be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et. al: Pharmazeutische Technologie, Thieme-Verlag, Stuttgart, 1978). The administration forms obtained in this way normally contain from 1 to 99% by weight of active ingredient.

The substances of the formula II to VI required as starting materials for synthesizing the novel compounds are known or can be synthesized from similar starting materials by preparation methods described in the literature (F. Sauter and P. Stanetty, Monatsh. Chem. 106(5), (1975), 1111–1116; K. Gewald et al., Chem. Ber. 99, (1966) 94–100, German patent application 196 36769.7).

The novel compounds have a high affinity for $5\text{-HT}_{1B}$, $5\text{-HT}_{1D}$ and $5\text{-HT}_{1A}$ serotonin receptors. The affinity for these receptors is moreover about the same, at least of the same order of magnitude. Furthermore, some of the novel compounds show good serotonin reuptake inhibition, a principle which is implemented in most antidepressants.

These compounds are suitable as drugs for treating pathological states in which the serotonin concentration is reduced and in which, as part of therapy, it is wished to block specifically the activity of the presynaptic $5\text{-HT}_{1B}$, $5\text{-HT}_{1A}$, $5\text{-HT}_{1D}$ receptors without having a great effect on other receptors too. An example of a pathological state of this type is depression.

The compounds of the present invention may also be useful for treating mood disorders with a central nervous causation, such as seasonal affective disorders and dysthymia. These also include anxiety states such as generalized anxiety, panic attacks, sociophobia, obsessive-compulsive neuroses and post-traumatic stress symptoms, memory disturbances including dementia, amnesias and age-related memory loss, and psychogenic eating disorders such as anorexia nervosa and bulimia nervosa.

The novel compounds can additionally be useful for treating endocrine disorders such as hyperprolactinemia and for treating vasospasms (especially of the cerebral vessels), hypertension and gastrointestinal disorders associated with motility and secretion disturbances. Another area of use comprises sexual disorders.

Some compounds also have an affinity for the 5-HT$_7$ receptor and could therefore be suitable for treating psychotic disorders such as schizophrenia and manic depressive psychoses or sleeping disorders.

The following examples serve to illustrate the invention:

A PREPARATION OF THE STARTING MATERIALS a) 2-Amino-3-carboethoxy-5-ethyl-4,5,6,7-tetrahydrothieno[3,2-c]pyridine 62.9 ml (588 mM [sic]) of ethyl cyanoacetate and 18.8 g (588 mM [sic]) of sulfur powder were added to 96.1 g (588 mM [sic]) of 1-ethyl-3-piperidone×HCl in 350 ml of ethanol and then, while stirring vigorously and under a nitrogen atmosphere, 150 ml (1080 mM [sic]) of triethylamine were added dropwise. After 0.5 h, the mixture was refluxed for 6 h and then left to stir at room temperature overnight. The reaction mixture was poured into 3 l of ice-water, adjusted to pH=9 and extracted twice with methylene chloride. The organic phase was dried and concentrated, and the crude product was purified by column chromatography (silica gel, eluent methylene chloride/methanol 93/7). 29.2 g (20%) of product were isolated as a slightly oily solid.

b) 2-Ethoxymethyleneamino-3-carboethoxy-5-ethyl-4,5,6,7-tetrahydrothieno[3,2-c]pyridine 0.5 ml of acetic anhydride was added to 3.8 g (14.9 mM [sic]) of 2-amino-3-carboethoxy-5-ethyl-4,5,6,7-tetrahydrothieno[3,2-c]pyridine in 40 ml of triethyl orthoformate and refluxed under nitrogen for 1 h. The solution was decanted off from the insoluble black deposit on the walls of the flask and then completely evaporated in a rotary evaporator at 80° C. 3.5 g (94%) of crude product were isolated as a dark oil which is sufficiently pure for further reaction.

The 5-acetyl derivatives were prepared from 1-acetyl-3-piperidone (P. Krogsgaard-Larsen, H. Hjeds: Acta Chem. Scand B 30 (1976) 884) in a similar manner to a) and b).

c) 3-(2-Hydroxyethyl)-6-ethyl-3,4,5,6,7,8-hexahydropyrido[3',4':4,5]thieno[2,3-d]pyrimidin-4-one 5.0 ml (81 mM [sic]) of ethanolamine were added to 17.0 g (55 mM [sic]) of 2-ethoxymethyleneamino-3-carboethoxy-5-ethyl-4,5,6,7-tetrahydrothieno[3,2-c]pyridine in 130 ml of ethanol and then refluxed for 2 h. The mixture was then concentrated to a volume of about 50 ml and stirred in an ice bath. The precipitated fine solid was filtered off with suction and washed with cold ethyl acetate. 10.5 g (63%) of pale brown product were isolated.

d) 3-(2-Chloroethyl)-6-ethyl-3,4,5,6,7,8-hexahydropyrido[3',4':4,5]thieno[2,3-d]pyrimidin-4-one 10.5 g (37.6 mM [sic]) of 3-(2-hydroxyethyl)-6-ethyl-3,4,5,6,7,8-hexahydropyrido[3',4':4,5]thieno-[2,3-d]pyrimidin-4-one in 100 ml of 1,2-dichloroethane were heated to reflux (slow dissolution) and then 3.5 ml (48 mM [sic]) of thionyl chloride in 20 ml of 1,2-dichloroethane were added dropwise. After refluxing for 1 h, the reaction mixture was allowed to cool, and the solid was filtered off with suction and washed with 1,2-dichloroethane. The crude product was partitioned between methylene chloride and water at pH=9. The organic phase was dried and concentrated to isolate 9.3 g (83%) of product as a dark oil which slowly crystallized and is sufficiently pure for further reactions, melting point 94–96° C.

e) N-(1-Naphthyl)piperazine 83.2 g (966 mM [sic]) of piperazine, 38.0 g (339 mM [sic]) of potassium tert-butoxide and 50.0 g (2.41 mM [sic]) of 1-bromonaphthalene were added to a mixture of 5.4 g (24.2 mM [sic]) of palladium acetate and 14.7 g (48.3 mM [sic]) of tri-o-tolylphosphine in 500 ml of xylene, and the mixture was refluxed while stirring vigorously under a nitrogen atmosphere for 10 h. The mixture was then diluted with methylene chloride, the insoluble residues were filtered off, and the filtrate was concentrated. The crude product was purified by column chromatography (silica gel, eluent, THF/methanol/ammonia 85/13/2). 21.5 g (42%) of product were isolated with melting point 84–86° C.

f) N-(2-Methyl-1-naphthyl)piperazine 14.7 g (82.7 mM [sic]) of bis(2-chloroethyl)amine×HCl were added to 13.0 g (82.7 mM [sic]) of 1-amino-2-methylnaphthalene in 100 ml of chlorobenzene and refluxed under nitrogen for 90 h. The mixture was then concentrated and partitioned between methylene chloride and water at pH=9, and the organic phase was dried and concentrated. The crude product was purified by column chromatography (silica gel, eluent/THF/methanol/ammonia 85/13/2. 11.6 g (62%) of product were isolated.

g) 4-piperazin-1-yl-isoquinoline 4.51 g (21.7 mM [sic]) of 4-bromoisoquinoline, 4.65 g (25.0 mM [sic]) of t-butyl piperazine-N-carboxylate, 0.1 g (0.11 mM [sic]) of tris(dibenzylideneacetone) dipalladium, 0.11 g (0.18 mM [sic]) of 2,2'-bis(diphenylphosphino)-1,1'-binaphthyl and 2.92 g (30.4 mm [sic]) of sodium t-butoxide were mixed in 50 ml of toluene and stirred at 75° C. for 2 h. The reaction mixture was added to ice/sodium chloride and extracted with ethyl acetate, the organic phase was dried over sodium sulfate and the solvent was removed in a rotary evaporator. The product crystallized and was filtered off with suction and washed with pentane. 5.5 g (81%) of the Boc-protected piperazine (melting point: 111° C.) were obtained. 5.2 g (16.6 mM [sic]) of this substance were taken up in 17 ml of dichloromethane and, at 0° C., taken up slowly with 17 ml of dichloromethane [sic] and, at 0°, 17 ml (0.22 mM [sic]) of trifluoroacetic acid were slowly added. The mixture was left to stir at 0° C. for 4 h, poured into ice-water and extracted with dichloromethane. The aqueous phase was filtered, made alkaline and extracted with dichloromethane. Drying over sodium sulfate and substantial removal of the solvent were followed by dilution with diethyl ether and precipitation of the hydrochloride with ethereal hydrochloric acid. 3.2 g (67%) of the product were obtained with melting point 293–294° C.

Further piperazine derivatives (see Examples) not disclosed in the literature (cf. also German Patent Application 19636769.7) were prepared as in e), f) and g).

B PREPARATION OF THE FINAL PRODUCTS

EXAMPLE 1

3,4,5,6,7,8-Hexahydro-6-ethyl-3-[2-(4-(2-methoxyphenyl)-1-piperazinyl)ethyl]pyrido[3',4':4,5]thieno[2,3-d]pyrimidin-4-one×3 HCl×2H$_2$O 2.3 g (10.0 mM [sic]) of 1-(2-aminoethyl)-4-(2-methoxyphenyl)piperazine were added to 3.1 g (10.0 mM [sic]) of 2-ethoxymethyleneamino-3-carboethoxy-5-ethyl-4,5,6,7-tetrahydrothieno[3,2-c]pyridine in 50 ml of ethanol and refluxed for 1 h. The mixture was then concentrated in a rotary evaporator, and the crude product was purified by column chromatography (silica gel, eluent methylene chloride/methanol 93/7). After conversion into the hydrochloride in ethyl acetate, 2.9 g (48%) of product were isolated with melting point 172–174° C.

EXAMPLE 2

3,4,5,6,7,8-Hexahydro-6-ethyl-3-[2-(4-(2-methoxy-1-naphthyl)-1-piperazinyl)ethyl]pyrido[3',4':4,5]thieno[2,3-d]pyrimidin-4-one×2 HCl×2 H$_2$O 1.3 g (4.5 mM [sic]) of N-(2-methoxy-1-naphthyl)piperazine and 0.65 g (4.5 mmol) of finely powdered potassium carbonate were added to 1.1 g (4.5 mM [sic]) of 3-(2-chloroethyl)-6-ethyl-3,4,5,6,7,8-hexahydropyrido[3',4':4,5]thieno[2,3-d]pyrimidin-4-one in 40 ml of xylene and refluxed under a nitrogen atmosphere for a total of 70 h. The mixture was then concentrated under reduced pressure, and the residue was partitioned at pH=10 between methylene chloride and water. The organic phases were dried and concentrated, and the crude product was purified by column chromatography (silica gel, eluent acetone). 1.1 g (50%) of product were isolated with melting point 232–234° C. (decompositon).

The following were prepared as in examples 1 and 2:

3. 3,4,5,6,7,8-Hexahydro-6-ethyl-3-[2-(4-(2-methyl-1-naphthyl)-1-piperazinyl)ethyl]pyrido[3',4':4,5]thieno[2,3-d]pyrimidin-4-one×2 HCl×3 H$_2$O, melting point 238–240° C. (decomposition)
4. 3,4,5,6,7,8-Hexahydro-6-ethyl-3-[2-(4-(1-naphthyl)-1-piperazinyl)ethyl]pyrido[3',4':4,5]thieno[2,3-d]pyrimidin-4-one×2 HCl×3 H$_2$O, melting point 298–300° C. (decomposition)
5. 3,4,5,6,7,8-Hexahydro-6-ethyl-3-[2-(4-(2-methylphenyl)-1-piperazinyl)ethyl]pyrido[3',4':4,5]thieno[2,3-d]pyrimidin-4-one
6. 3,4,5,6,7,8-Hexahydro-6-ethyl-3-[2-(4-(2,3-dimethylphenyl)-1-piperazinyl)ethyl]pyrido[3',4':4,5]thieno[2,3-d]pyrimidin-4-one
7. 3,4,5,6,7,8-Hexahydro-6-ethyl-3-[2-(4-(2-chlorophenyl)-1-piperazinyl)ethyl]pyrido[3',4':4,5]thieno[2,3-d]pyrimidin-4-one, melting point 148–150° C.
8. 3,4,5,6,7,8-Hexahydro-6-ethyl-3-[2-(4-pyrimidin-2-yl-1-piperazinyl)ethyl]pyrido[3',4':4,5]thieno[2,3-d]pyrimidin-4-one
9. 3,4,5,6,7,8-Hexahydro-6-ethyl-3-[2-(4-pyridin-2-yl-1-piperazinyl)ethyl]pyrido[3'4':4,5]thieno[2,3-d]pyrimidin-4-one
10. 3,4,5,6,7,8-Hexahydro-6-ethyl-3-[2-(4-quinolin-2-yl-1-piperazinyl)ethyl]pyrido[3',4':4,5]thieno[2,3-d]pyrimidin-4-one
11. 3,4,5,6,7,8-Hexahydro-6-ethyl-3-[2-(4-(2-methoxyphenyl)-1-piperidinyl)ethyl]pyrido[3',4':4,5]thieno[2,3-d]pyrimidin-4-one
12. 3,4,5,6,7,8-Hexahydro-6-ethyl-3-[2-(4-(2-methoxyphenyl)-3,4-dehydro-1-piperidinyl)ethyl]pyrido[3',4':4,5]thieno[2,3-d]pyrimidin-4-one
13. 3,4,5,6,7,8-Hexahydro-6-ethyl-3-[3-(4-pyrimidin-2-yl-1-piperazinyl)propyl]pyrido[3',4':4,5]thieno[2,3-d]pyrimidin-4-one×3 HCl×4H$_2$O, melting point 211–213° C. (decomposition)
14. 3,4,5,6,7,8-Hexahydro-6-ethyl-3-[2-(4-tetralin-5-yl-1-piperazinyl)ethyl]pyrido[3',4':4,5]thieno[2,3-d]pyrimidin-4-one, melting point 287° C. (hydrochloride)
15. 3,4,5,6,7,8-Hexahydro-6-ethyl-3-[2-(4-indan-1-yl-1-piperazinyl)ethyl]pyrido[3',4':4,5]thieno[2,3-d]pyrimidin-4-one 16. 3,4,5,6,7,8-Hexahydro-6-ethyl-3-[2-(4-(3-trifluoromethylphenyl)1-piperazinyl)ethyl]pyrido[3',4':4,5]thieno[2,3-d]pyrimidin-4-one
17. 3,4,5,6,7,8-Hexahydro-6-ethyl-3-[2-(4-(2-cyanophenyl)-1-piperazinyl)ethyl]pyrido[3',4':4,5]thieno[2,3-d]-pyrimidin-4-one
18. 3,4,5,6,7,8-Hexahydro-6-ethyl-3-[2-(4-isoquinolin-4-yl-1-piperazinyl)ethyl]pyrido[3',4':4,5]thieno[2,3-d]-pyrimidin-4-one
19. 3,4,5,6,7,8-Hexahydro-6-ethyl-3-[2-(4-naphth-1-yl-hexahydro-1,4-diazepin-1-yl)ethyl]pyrido[3',4':4,5]thieno[2,3-d]-pyrimidin-4-one, melting point 276–280° C. (hydrochloride)
20. 3,4,5,6,7,8-Hexahydro-6-ethyl-3-[2-(4-naphth-1-yl-3,4-dehydro-1-piperidinyl)ethyl]pyrido[3',4':4,5]thieno-[2,3-d]-pyrimidin-4-one, MS: m$^+$=507.1
21. 3,4,5,6,7,8-Hexahydro-6-ethyl-3-[2-(4-naphth-1-yl-1-piperidinyl)ethyl]pyrido[3',4': 4,5]thieno-[2,3-d]-pyrimidin-4-one
22. 3,4,5,6,7,8-Hexahydro-6-ethyl-3-[2-(4-(2-methoxy-1-naphthyl-3,4-dehydro-1-piperidinyl)ethyl]pyrido[3',4':4,5]thieno[2,3-d]-pyrimidin-4-one
23. 3,4,5,6,7,8-Hexahydro-6-acetyl-3-[2-(4-(2-methoxyphenyl)-1-piperazinyl)ethyl]pyrido[3',4':4,5]thieno[2,3-d]-pyrimidin-4-one
24. 3,4,5,6,7,8-Hexahydro-6-acetyl-3-[2-(4-(2-methyl-1-naphthyl)-1-piperazinyl)ethyl]pyrido[3',4':4,5]thieno[2,3-d]-pyrimidin-4-one
25. 3,4,5,6,7,8-Hexahydro-6-acetyl-3-[2-(4-(2-methoxy-1-naphthyl)1-piperazinyl)ethyl]pyrido[3',4':4,5]thieno[2,3-d]-pyrimidin-4-one The acetyl group in position 6 can be eliminated as described in DE 19 636 769.7 with 10 percent hydrochloric acid under reflux to give the corresponding secondary amines. Alkylations on N-6 to give the 6-alkyl derivatives can likewise be carried out as described in DE 19 636 769.7.

26. 3,4,5,6,7,8-Hexahydro-3-[2-(4-(2-methoxyphenyl)-1-piperazinyl)ethyl]pyrido[3',4':4,5]thieno[2,3-d]pyrimidin-4-one
27. 3,4,5,6,7,8-Hexahydro-6-benzyl-3-[2-(4-(2-methylphenyl)-1-piperazinyl)ethyl]pyrido[3',4':4,5]thieno[2,3-d]pyrimidin-4-one
28. 3,4,5,6,7,8-Hexahydro-6-(4-chlorophenyl-2-ethyl)-3-[2-(4-(1-naphthyl)-1-piperazinyl)ethyl]pyrido[3',4':4,5]thieno[2,3-d]pyrimidin-4-one
29. 3,4,5,6,7,8-Hexahydro-6-(4-methoxybenzyl)-3-[2-(4-(2-methyl-1-naphthyl)-1-piperazinyl)ethyl]pyrido[3',4':4,5]thieno[2,3-d]pyrimidin-4-one
30. 3,4,5,6,7,8-Hexahydro-6-ethyl-3-[3-(4-phenyl-1-piperidinyl)-propyl]pyrido[3',4':4,5]thieno[2,3-d]pyrimidin-4-one, melting point 241° C. (hydrochloride)

We claim:
1. A 3-substituted 3,4,5,6,7,8-hexahydropyrido[3',4':4,5]thieno-[2,3-d]pyrimidine derivative of the formula I

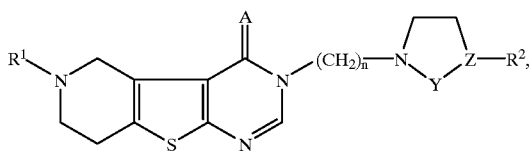

where
- $R^1$ is a hydrogen atom, a $C_1$–$C_4$-alkyl group, an acetyl group, a phenylalkyl $C_1$–$C_4$ radical, the aromatic system being unsubstituted or substituted by halogen, $C_1$–$C_4$-alkyl, trifluoromethyl, hydroxyl, $C_1$–$C_4$-alkoxy, amino, cyano or nitro groups, or is a phenylalkanone radical, it being possible for the phenyl group to be substituted by halogen,
- $R^2$ is a phenyl, pyridyl, pyrimidinyl or pyrazinyl group which is unsubstituted or mono- or disubstituted by halogen atoms, $C_1$–$C_4$-alkyl, trifluoromethyl, trifluoromethoxy, hydroxyl, $C_1$–$C_4$-alkoxy, amino, monomethylamino, dimethylamino, cyano or nitro groups and which may be fused to a benzene nucleus which can be unsubstituted or mono- or disubstituted by halogen atoms, $C_1$–$C_4$-alkyl, hydroxyl, trifluoromethyl, $C_1$–$C_4$-alkoxy, amino, cyano or nitro groups and may contain 1 nitrogen atom, or to a 5- or 6-membered ring which may contain 1–2 oxygen atoms,
- A is NH or an oxygen atom,
- Y is $CH_2$, $CH_2$—$CH_2$, $CH_2$—$CH_2$—$CH_2$ or $CH_2$—$CH$,
- Z is a nitrogen atom, carbon atom or CH, it also being possible for the linkage between Y and Z to be a double bond,
- and n is 2, 3 or 4, and the physiologically tolerated salts thereof.

2. A compound as claimed in claim 1, wherein
- $R^1$ is methyl, ethyl, benzyl
- $R^2$ is o-methoxyphenyl, 1-naphthyl, 2-methoxy-1-naphthyl, 2-methyl-1-naphthyl
- A is an oxygen atom
- Y is $CH_2$—$CH_2$
- Z is a nitrogen atom
- and n is 2 and 3.

3. A pharmaceutical composition containing as the active ingredient a compound as claimed in claim 1.

4. A method of treating depression comprising administering an effective amount of a composition as claimed in claim 3.

5. A method of increasing serotonin concentration in the brain of a patient in need of such treatment comprising administering an effective amount of a composition as claimed in claim 3.

6. The method of claim 5, wherein serotonin reuptake inhibition and/or selective serotonin antagonism is effected.

7. A method of treating mood disorders, psychogenic eating disorders, endocrine disorders, sexual disorders, gastrointestinal disorders, schizophrenia or manic depressive psychosis comprising administering an effective amount of a composition as claimed in claim 3.

* * * * *